Figure 1:
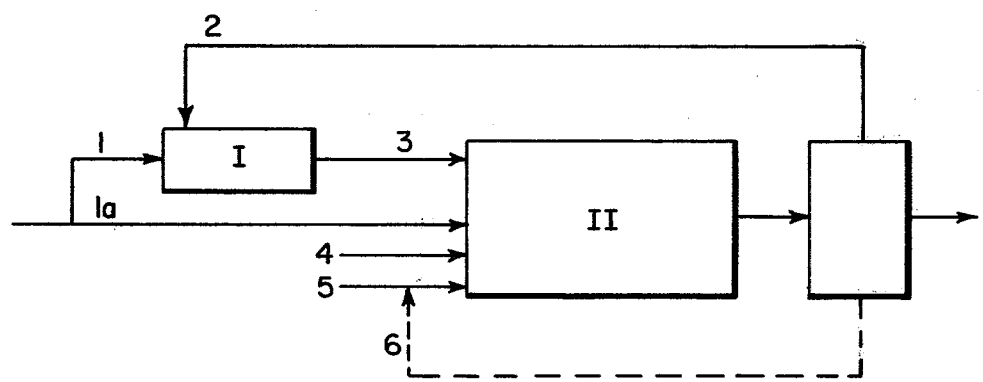

United States Patent [19]

Datow et al.

[11] 4,213,919

[45] Jul. 22, 1980

[54] MANUFACTURE OF β-CHLOROCARBOXYLIC ACID CHLORIDES

[75] Inventors: Joachim Datow; Martin Decker; Karl Merkel, all of Ludwigshafen; Franz Neumayr, Weisenheim am Berg, all of Fed. Rep. of Germany

[73] Assignee: BASF Aktiengesellschaft, Fed. Rep. of Germany

[21] Appl. No.: 959,834

[22] Filed: Nov. 13, 1978

Related U.S. Application Data

[63] Continuation of Ser. No. 755,855, Dec. 30, 1976, abandoned.

[51] Int. Cl.$^2$ ............................................. C07C 51/58
[52] U.S. Cl. ............................ 260/544 K; 562/493; 562/603
[58] Field of Search ........................ 260/544 K, 539 R; 562/405, 493, 603

[56] References Cited

U.S. PATENT DOCUMENTS

| 2,759,018 | 8/1956 | Opfermann | 260/539 R |
|---|---|---|---|
| 2,774,785 | 12/1956 | Wystrach | 260/539 R |
| 2,848,491 | 8/1958 | Mackenzie et al. | 260/544 K |
| 3,149,155 | 9/1964 | Siefelder | 260/544 K |
| 3,544,627 | 12/1970 | Carr et al. | 260/544 K |
| 3,547,960 | 12/1970 | Hauser | 260/544 K |
| 3,857,841 | 12/1974 | Keil | 260/544 K |

*Primary Examiner*—Norman Morgenstern
*Attorney, Agent, or Firm*—Keil & Witherspoon

[57] ABSTRACT

The manufacture of β-chlorocarboxylic acid chlorides by reacting αβ-olefinically unsaturated carboxylic acids with phosgene is advantageously carried out by first at least partially reacting the unsaturated carboxylic acid with hydrogen chloride and then carrying out the reaction with phosgene.

4 Claims, 2 Drawing Figures

MANUFACTURE OF β-CHLOROCARBOXYLIC ACID CHLORIDES

This is a continuation of application Ser. No. 755,855, filed Dec. 30, 1976, now abandoned.

The manufacture of carboxylic acid chlorides from the corresponding acids and an inorganic acid chloride, e.g. $PCl_3$, $SOCl_2$ or $COCl_2$, has been disclosed.

In the case of certain inorganic acid chlorides, this reaction requires a catalyst. Compounds from the group of the disubstituted acid amides have proved suitable catalysts; they form, with the inorganic acid chlorides, compounds which can be isolated and are called Vilsmeier complexes; it is these which bring about the actual reaction. In the case of phosgene this may be represented by the following equations:

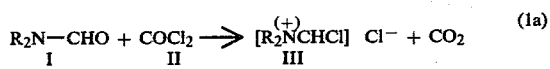

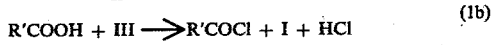

In actual operation, the acid is mixed with the acid amide and this mixture is allowed to react with excess phosgene at below 100° C.

In principle, α,β-unsaturated carboxylic acids undergo the same reaction, but the hydrogen chloride formed immediately reacts further and adds onto the double bond, to form the β-chloro compound (2):

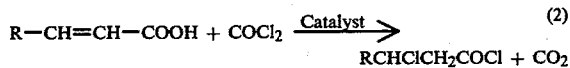

Since β-chlorocarboxylic acid chlorides are industrially of interest as intermediate products, this process is used on an industrial scale.

U.S. Pat. No. 3,149,155 discloses that the reaction of acrylic acid with phosgene, using dimethylformamide as the catalyst, gives β-chloropropionic acid chloride in a yield of 84% (after distillation). It has also been observed that a substantial amount of non-volatile residue remains. This, incidentally, is also true of other α,β-unsaturated carboxylic acids. It must be assumed that the residue forms as a result of polymerization of the acrylic acid, first introduced into the reaction vessel, under the reaction conditions.

It is an object of the present invention to provide a process by means of which the catalytic reaction of phosgene and an α, β-unsaturated carboxylic acid, to form a β-chlorocarboxylic acid chloride, can be carried out with improved yields and with the formation of less residue.

We have found that this object is achieved by reacting the olefinically unsaturated carboxylic acid, in a first stage, at least partially with hydrogen chloride and carrying out the reaction with phosgene in a second stage. Accordingly, the reaction takes place in two stages. For example, following the scheme in FIG. 1, acrylic acid (1) is first partially reacted with hydrogen chloride (2) to give β-chloropropionic acid (3); in the second stage, after addition of the catalyst (4), acrylic acid (1a) and phosgene (5) are passed simultaneously into the chloropropionic acid formed, which is kept at an elevated temperature. Advantageously, the amounts used are such that at the end of the reaction there is an excess of phosgene present in the mixture, and this is recovered (6). The process can be carried out continuously or batchwise.

The process may be used for the manufacture of β-chlorocarboxylic acid chlorides; examples of compounds of particular industrial importance are the corresponding chlorinated derivatives of propionic acid, n- and iso-butyric acid, ethylhexanoic acid and other fatty acids, as well as substituted fatty acids, e.g. 3-phenylpropionic acid. The carboxylic acids and their derivatives as a rule have from 3 to 10 carbon atoms in the molecule and are in general known.

The reaction of the unsaturated carboxylic acid with hydrogen chloride in many cases taken place even at room temperature; in general, an adequate rate of reaction is achievable by moderate heating. A catalyst is not required for this reaction step.

Figure 2:
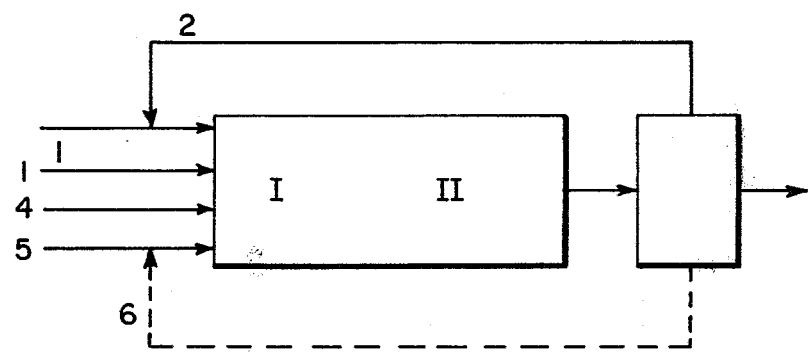

Advantageously, at least 5 mole per cent of the unsaturated carboxylic acid to be converted are initially reacted with hydrogen chloride; in general, a conversion of less than 40%, for example of from 10 to 25%, suffices, after which the remaining amount of the unsaturated carboxylic acid together with the β-chlorocarboxylic acid already formed can be reacted directly with phosgene. It is also possible first to react the unsaturated carboxylic acid completely with hydrogen chloride. The hydrogen chloride liberated in the second stage, at a reaction temperature of, for example, from 40 to 100° C., can be used for the reaction in the first stage, if the production plant available is suitably equipped. As a rule, gaseous hydrogen chloride is allowed to act on the carboxylic acid, without the use of additional solvents. Sometimes it is advantageous to bring the carboxylic acid (1) into contact with hydrogen chloride (2) and phosgene (5) simultaneously in the first stage; since the addition reaction of hydrogen chloride takes place very rapidly, this embodiment also constitutes an example of the process of the invention (FIG. 2). It follows that in this latter case an excess of hydrogen chloride is maintained in the equipment provided for the reaction since, per mole of phosgene reacted, one mole of hydrogen chloride is liberated, which can be recovered and accordingly it is merely necessary to have a certain amount of hydrogen chloride available at the start of the reaction, in order to initiate the latter. This amount should obviously be, for example, from 5 to 40 mole %, or more, of the total amount of carboxylic acid present in the equipment at the same time.

In general, the reaction takes place without requiring superatmospheric pressure, i.e. it is carried out under atmospheric pressure. In that case, the equipment used can advantageously be made of glass. However, especially where the addition reaction of hydrogen chloride is concerned, the reaction can also be carried out under moderate pressure, e.g. of up to 5 bars.

As mentioned at the outset, the reaction with phosgene is catalyzed by certain acid amides; examples of suitable compounds are dialkylamides of the type of dimethylformamide, i.e. dialkylformamides and corresponding cyclic amides, i.e. N-formylalkyleneimines, e.g. N-formylpyrrolidine. These amides are used in catalytic amounts, e.g. of up to 5%, based on phosgene.

EXAMPLE 1

525 kg of acrylic acid are introduced into a kettle and 290 kg of anhydrous hydrogen chloride are passed in at 45° C., whilst cooling. When the reaction has subsided, 20 kg of dimethylformamide are added, and 4,000 kg of phosgene and 2,100 kg of acrylic acid are then metered into the reaction mixture at from 60° to 70° C. at a rate such that the addition of both components is terminated simultaneously. When all has been added, the excess phosgene is removed. 4,650 kg of technical-grade β-chloropropionic acid chloride are obtained; this material can be used directly for further syntheses.

On distilling a sample of 100 parts of this crude product (at 27 mbar and 60° C.), 99.2 parts of a water-white liquid are obtained; analysis shows this material to contain 0.5 part of acrylic acid chloride and to be 99.4% pure.

EXAMPLE 2

In carrying out the reaction continuously, acrylic acid was first reacted with less than the stoichiometric amount of hydrogen chloride in a pre-reactor, and the mixture was then reacted with phosgene. Excess phosgene is removed under reduced pressure in a downstream column.

Using the arrangement shown schematically in FIG. 2, 192.4 kg per hour of acrylic acid are mixed with 6 kg per hour of dimethylformamide in a stirred vessel which serves as a prereactor, and 24 kg of anhydrous hydrogen chloride per hour are passed in at 45° C. The reaction mixture which issues is reacted, without further treatment, with 293 kg of phosgene per hour in a stirred vessel, which serves as the main reactor, at from 60° to 65° C.

After removing the excess phosgene, 350 kg per hour of a crude product are obtained; on distillation in stages, this material left 4.0 percent by weight of non-volatile residue. The distillate still contained 1.4 percent by weight of acrylic acid chloride. The yield is 98% of the stoichiometric amount.

EXAMPLE 3

The reaction was carried out in the same apparatus, and in the same manner, as described in Example 2, except that the gaseous hydrogen chloride was introduced directly into the main reactor together with the phosgene. The product obtained in this way contained 6.5 percent by weight of non-volatile residue and the distillate contained 1.8 percent by weight of acrylic acid chloride. The yield is 95% of the stoichiometric amount.

COMPARISON WITH EXAMPLE 3

The reaction was carried out in the same apparatus, with the same amounts and under the same conditions, except that no hydrogen chloride was employed. The product contained 12.5 percent by weight of non-distillable residue and 3.5 percent by weight of acrylic acid chloride. The yield is 87% of the stoichiometric amount.

We claim:
1. A process for the manufacture of a β-chlorocarboxylic acid chloride by the catalytic reaction of phosgene and an α,β-unsaturated carboxylic acid which comprises:
    (a) in a first stage, reacting from about 5 to 40 mole % of the α,β-unsaturated carboxylic acid with hydrogen chloride in the absence of added solvents, and
    (b) in a second stage, reacting the first stage reaction mixture with phosgene in the presence of an effective amount of a catalyst.
2. A process as set forth in claim 1, wherein, in the second stage, a stoichiometric excess of phosgene is employed and a reaction temperature of from 40° to 100° C. is maintained.
3. A process as set forth in claim 1, wherein β-chloropropionic acid chloride is formed using acrylic acid as a reactant.
4. A process as set forth in claim 1, wherein the catalyst is an acid amide.

* * * * *